US012758439B2

(12) United States Patent
Fancher

(10) Patent No.: US 12,758,439 B2
(45) Date of Patent: Oct. 13, 2026

(54) LIMB AND TORSO COVER WITH ELASTIC CLOSURE

(71) Applicant: Rebecca Ann Treadway Fancher, West Monroe, LA (US)

(72) Inventor: Rebecca Ann Treadway Fancher, West Monroe, LA (US)

( * ) Notice: Subject to any disclaimer, the term of this patent is extended or adjusted under 35 U.S.C. 154(b) by 417 days.

(21) Appl. No.: 18/149,053

(22) Filed: Dec. 30, 2022

(65) Prior Publication Data

US 2024/0238126 A1 Jul. 18, 2024

(51) Int. Cl.
*A61F 15/00* (2006.01)
*A41D 19/00* (2006.01)
*A61F 13/01* (2024.01)

(52) U.S. Cl.
CPC ........ *A61F 15/004* (2013.01); *A41D 19/0055* (2013.01); *A61F 13/01017* (2024.01); *A61F 13/01029* (2024.01)

(58) Field of Classification Search
CPC .................. A61F 15/004; A61F 15/008; A61F 13/01017; A61F 13/01029; A61F 15/00; A61F 13/041; A61F 13/043; A61B 46/20; A61B 46/27; A61B 42/00; A61B 42/10; A61B 42/20; A41D 13/08; A41D 13/081; A41D 13/087; A41D 19/015
USPC ................................................................ 602/3
See application file for complete search history.

(56) References Cited

U.S. PATENT DOCUMENTS 5,643,183 A * 7/1997 Hill ........................ A61F 15/004 602/3
2001/0041853 A1* 11/2001 South .................... A61F 15/004 602/3
2003/0065357 A1* 4/2003 Dedo ................ A61B 17/1322 606/203
2004/0199974 A1* 10/2004 Fancher .................. A61F 13/06 2/59
2006/0010564 A1* 1/2006 Villarreal ........... A41D 19/0055 2/161.7
2011/0087144 A1* 4/2011 Lee ....................... A61F 15/002 602/3
2017/0335086 A1* 11/2017 Leano ...................... C08K 5/29
2020/0289334 A1* 9/2020 Choudhury ............. A61F 13/60
2021/0069035 A1* 3/2021 Cottrell ................. A61F 15/008

* cited by examiner

*Primary Examiner* — Rachael E Bredefeld
*Assistant Examiner* — Seth R. Brown

(57) ABSTRACT

An elasticized protective covering for limb or torso, comprising self-encased elastic band or bands integrated at the open end or ends of the cover, made of proprietary polymeric material to offer simple, effective and affordable protection for areas of concern and healing sites and prevention of contamination and infection throughout treatment and recovery while maintaining daily hygiene for bathing or showering and eliminating the need for cumbersome and constricting straps, tourniquets, adhesives, Velcro, drawstring or gasket closures.

8 Claims, 3 Drawing Sheets

LIMB AND TORSO COVER WITH ELASTIC CLOSURE

CROSS-REFERENCE TO RELATED APPLICATIONS

U.S. Pat. No. 7,290,290, to Treadway-Fancher
U.S. Pat. No. 1,639,945 to Betz
U.S. Pat. No. 4,178,924 to Baxter
US2009/0113591 Deutsch et al.
U.S. Pat. No. 7,955,284, Brown et al.

BACKGROUND OF THE INVENTION

In our ever-evolving world, contamination from bacteria, chemicals and pollution are prevalent and in the forefront of the future of medicine and workplace environments. Prevention is our next best cure, and keeping areas of concern free from contaminants is key in what we term, “infection control,” particularly for those in treatment for and recovering from medical conditions and procedures. It is well known and long accepted that water is one of the major causes of infection to individuals in such situations. Water used for bathing is known to carry bacteria that can cause or compound an existing problem or condition. Patients with an intravenous line (IV), peripherally inserted central catheter (PICC line) or undergoing dialysis treatments have direct lines into their bloodstreams, which make them particularly susceptible to infections from bacterial contamination. Those who wear a cast or have a dressing or wound share the same risk of contamination. Water that stays under a cast can result in a skin infection which creates a compound problem that hinders recovery. Water that contaminates a wound prolongs the healing process, or can possibly lead to further complications, such as secondary infections which can lead to amputation. An infection of a surgical site can cause a patient to return to the hospital for further treatment.

Showering is key to maintaining dignity and a level of acceptable hygiene to which all patients should be entitled. Ambulatory patients who have the ability to shower during their treatment and recover are often left to their own creativity to fashion protective devices for their areas of concern.

Garbage bags and tape or rubber bands are the most popular forms of protection that will be implemented to attempt protection from damaging moisture. There are several reasons that garbage bags are not adequate for the purpose of keeping an area of concern dry during a showering process:

1) The size of the garbage bag, in most cases, is considerably larger in circumference than the limb it is to cover. The opening is then gathered around the limb and must be secured in some manner. If tape is applied to the bag opening to secure it to itself and to the limb, the individual may be at risk of not only inadequate protection, but creating another problem upon removing the adhesive, such as skin irritation or removal, resulting in another wound. Rubber bands may be applied, but are ineffective against the bulk of the gathers, which form water paths encouraging water entrance, rather than deflection.
2) Garbage bags are slippery, which hinders their use on wet surfaces and even creates a potential hazard for the wearer.
3) The enlarged, non-specifically sealed end of the bag, if placed over an arm, makes it difficult and ineffective to use the hand and fingers to assist in bathing.

Showering products currently on the market, with the exception of the present inventor’s patent, U.S. Pat. No. 7,290,290 B2, to Treadway-Fancher, are cumbersome, having a sealing ring gasket configuration, as in U.S. Pat. No. 4,639,945 to Betz, issued Feb. 3, 1987, or will compromise the area of concern by dragging the tight opening over the healing site or painful IV or PICC line, such as U.S. Patent application No. US2009/0113591 Deutsch et al. and U.S. Pat. No. 7,955,284, Brown et al. issued Jun. 7, 2011. Yet other inventions, such as U.S. Pat. No. 4,178,924 to Baxter, issued Dec. 18, 1979, include the use of a strap which is wrapped around the open end of the device numerous times, which can cause constriction of the limb to which it is applied.

Such complicated devices usually are costly to the consumer and individuals who use the item for a length of time may experience the product either becoming contaminated with mildew or bacteria from wound seepage or it may become ineffective from seam splits, tears along the tight slit entry opening or stretched out from excessive use until it is no longer effective. Most consumers will attempt to maximize the usage of such devices, especially if they are costly, and may either use a contaminated product, try to clean it ineffectively, or save the item for some unknown future use or for another individual to use. Again, this becomes an issue of concern with infection control.

Previously named inventions and other like products on the market consist of an open end and a distal end with the hand portion typically being formed in the shape of a mitten, having a thumb sleeve and a finger pocket, and the distal end of the leg device having a formed “foot” ending. Problems with such detailed distal ends are that the “mitten” end of an arm device does not allow for the wearer to perform normal bathing tasks, such as washing one’s hair or picking up shampoo bottles or soap, due to the fact that the finger pocket is excessively larger than a normal sized hand which will not allow the fingers to act independently. Even “gloved” designs are not effective, because the long finger sleeves are not large enough to accommodate heavily casted or bandaged fingers. The “footed” ends of the other leg devices are made excessively large to accommodate a variety of foot sizes, which creates a potential hazard for the wearer to trip while walking or moving around in a shower setting.

BRIEF SUMMARY OF THE INVENTION

The purpose of the present invention is to provide an improvement upon the previously issued patent U.S. Pat. No. 7,290,290 B2 to Treadway-Fancher, as well as to other patents pertaining to a protective moisture resistant showering device, and provide new and improved features of the original invention.

The current invention is to be considered as a re-usable disposable and made from a proprietary blend of polymeric material, with non-slip, durable and stretchable properties and may be made resistant to mildew and bacteria. The polymeric material consists of a higher grade polymer such as polyethylene, and at least 1.5 mil in thickness for durability. The stretchable property enhances the durability and longevity of the device for prolonged or indefinite uses. The non-slip property of the proprietary blend allows the user to safely move about on wet surfaces or to pick up and hold wet and slippery items used for showering, such as soap or shampoo bottles. The material may be made non-slip by adding known non-slip ingredients or by eliminating the slip property in the extrusion process. Anti-microbial properties also may be added into the blend.

The specially blended polymeric material will be extruded in tubular fashion to the dimensions specified for each product category made. Tubular film eliminates seams, which will eliminate seam splits which could render the item ineffective and useless. An unformed tube provides the same circumference the entire length of the section chosen to make a product. This allows the structure to accommodate the angle of the limb with cast or dressing without the constriction of formed or curved sides. A pre-set design, such as is required in the aforementioned invention by Brown concerning the "bump out" feature of his arm design and the formed footed portion of the leg design is unnecessary and not practical for free movement. The effort to pull a formed bent arm design over an arm that is in a cast is unrealistic and nearly impossible.

The tubular lengths of the present invention will be sealed at the distal end to accommodate a hand or a foot. Arm devices will be heat sealed, die-cut to resemble a combination of a mitten and a glove, with the roominess of a mitten, and shortened finger and thumb sleeves into fingertips and thumb tip portions. The desired effect is that of abbreviated digital pockets to contain only the fingertips and thumb tip while allowing the roominess of a mitten for the hand. The purpose of the shortened tips is to allow the wearer to actively use a bandaged or casted hand for the purpose of assisting in daily hygiene purposes in a shower setting and have the use of both hands. This hybrid concept of a glove and a mitten are unique and unknown to the industry. Existing hand/arm covers comprise a "mitten" or "glove" ending for which to place fingers and thumbs. In normal casting or in bandaging a hand, the fingers often are made larger by the cast or bandage and cannot fit adequately in a regular "glove" ending while the bulk of the "mitten" renders the use of the hand ineffective. The present invention allows the cast or bandage to have the room needed while making use of the unencumbered fingertips to aid in the bathing process.

The tubular leg device has a continuous diameter the length of the tube without a defined foot accommodation. The distal end is sealed with a multi-layer seal resulting in the width of the seal being less than half the diameter of the tubular material. This multi-layer seal helps to narrow the excess material at the distal end providing a feasible fitted feature to allow safe movement while wearing and sealing off the distal end to prevent water entry while in use. The continuous tubular design accommodates an unlimited number of foot sizes, including bulky bandages or casts. Previous inventions propose formed foot areas, which are not adequate if the foot is too big for the design or will be a danger of tripping the wearer if the foot is too small for the design.

The multi-layer seal provides a stronger seal than a regular heat seal/die cut in that with each layer or fold added, the seal becomes stronger. If the polymeric material is 1.5 mil, then folding it once makes the strength of the seal equal to 3 mil, folding it twice makes it four times as strong or equal to 6 mil, etc. Each folded layer adds to the durability of the invention for the foot/leg and also allows for easy folding for packaging. When the leg device is inflated, the seal itself presents in a rounded appearance, which is more feasible and appealing than an ordinary flat seal. This allows the wearer to don the device over a cast, surgical shoe, walking boot or regular footwear.

The open end of the device, whether with hand or foot ending, is an integrated elastic closure with either a single elastic band or two or more bands with a space between. The elastic band on the uppermost edge of the device is encased and sealed to form inward toward the limb and is placed to deflect the initial spray of water in a shower setting. Additional band or bands are placed a distance down from the top encased band, in an approximate 2" distance, and encased by sealing inward to form an inner ledge. The space between the multiple placed bands is used for added protection against moisture seeping into the device past the first placed elastic band. While the spacing is key to allowing the inner ledges to adequately form inward and aid in the capturing of moisture that may trickle past the first band, it also serves the purpose of receiving absorbent material to prevent any pooling water from dumping into the device upon removal. Absorbent material, such as paper toweling or thin facial-type cloths is recommended for insertion between the bands. This prevents moisture that has collected on the inner ledge from escaping into the interior of the device, keeping the area of concern dry throughout the showering process and in removal. In the case of centrally focused limb coverage, as for the mid-arm or mid-leg, the device has two open ends, with single or multiple encased elastic closures at each end.

The self-encased elastic closure of the present invention eliminates the need for outside tourniquet, drawstring, adhesive, Velcro or gasket closures. The simplicity of the distal ends allows the user the uncomplicated protection needed to maintain the integrity of their area of concern.

DETAILED DESCRIPTION OF THE INVENTION

Figure 1:
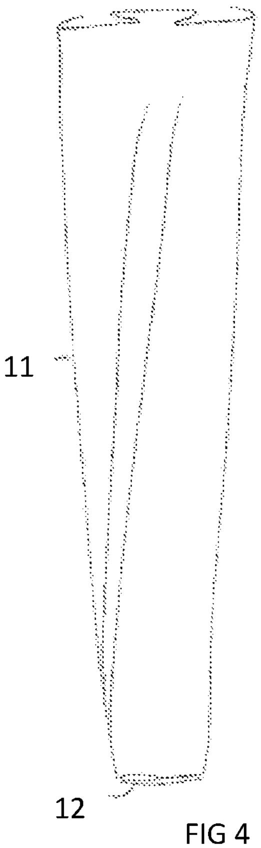
FIG. 1 illustrates tubular polymeric material folded and sealed at one end.
Figure 2:
FIG. 2 illustrates the embodiment of the present invention, being tubular polymeric material, sealed at one end and containing multiple encased elastic bands at the open end.
Figure 3:
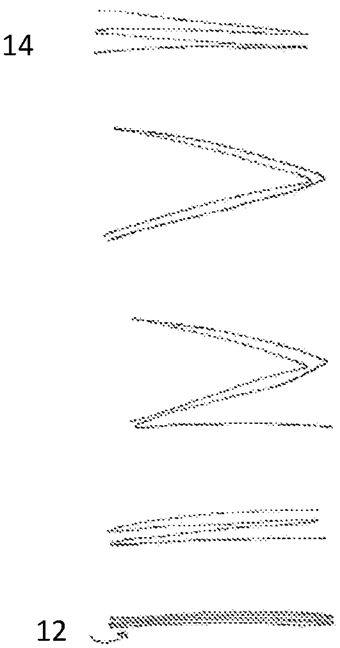
FIG. 3 shows examples of various multiple folds that can be sealed in a multi-layer seal which is used at the distal end of a leg device.
Figure 4:
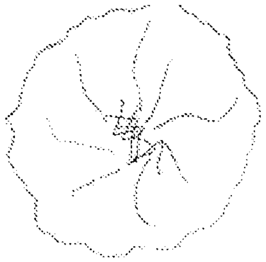
FIG. 4 is a perspective view of the bottom end seal, as the leg device is inflated with air.
Figure 6:
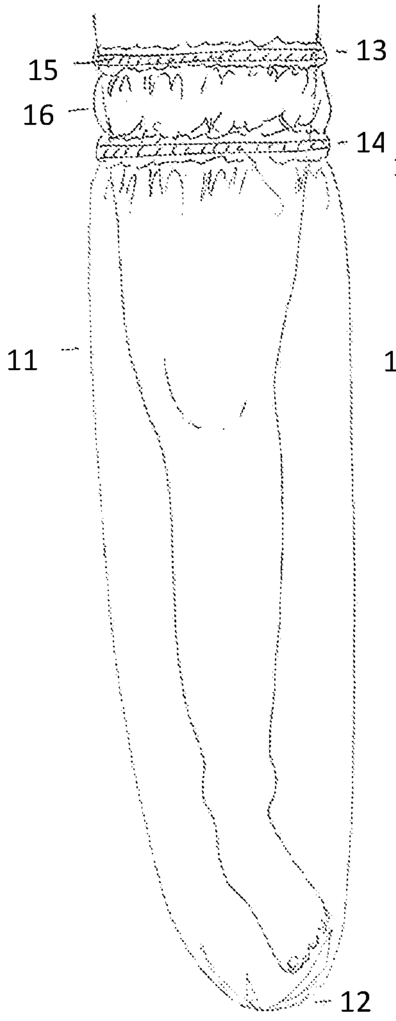
FIG. 6 illustrates a human limb schematically and in perspective to demonstrate the use of the device on a leg.

The present invention comprises an embodiment of tubular polymeric material, FIG. 1, 11, sealed at the closed distal end, 12, in a manner that creates a multi-layer seal, FIG. 3, which equals half or less than half of the diameter of the tubular material, and sealed at the open end with elastic bands, 15, encased at the open end, 13, and additional bands, 14, encased a distance parallel to the first band, at each open end, with a space between, FIG. 6, 16, in which to contain moisture which may pass through the first band, and allow for absorbent material to be placed between if needed.

Figure 5:
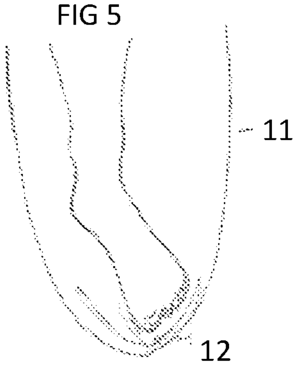
FIG. 5 is the view of a human leg in perspective to demonstrate the shape of the device after it is in place.

The sealed end may be comprised of various multi-layer folds, FIG. 3, which results n the reinforced end seal at the distal end of the leg devices, 12. This multi-layer folded seal allows for flat packaging of the device and provides a rounded appearance, FIG. 5, when pushed out with air by inflation or average wear.

Figure 7:
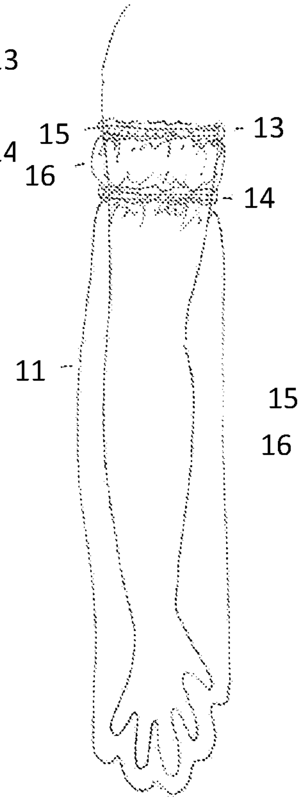
FIG. 7 illustrates a human limb schematically and in perspective to demonstrate the use of the device on an arm.

The tubular polymeric material may contain non-slip properties, which allow the wearer to stand or walk safely on wet surfaces, if using a leg device, or will allow the wearer to grasp wet or slippery grooming items during the course of bathing. If using an arm device with a distal end, FIG. 7. The material may be of a stretchable content, allowing for extended wear and durability for multiple uses. The polymeric material is cost effective and affordable for the wearer to purchase and to replace if device becomes contaminated with mildew or bacteria, which makes it a key recovery item for infection control purposes, yet is durable enough to be used multiple times throughout treatment and recovery, which meets current green and environmental standards, legislation and expectations. Anti-microbial agents also may be integrated into the polymeric material, which will help ensure a bacteria-free environment.

Figure 8:
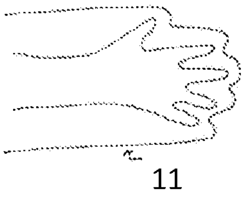
FIG. 8 is an in-focus view of the hand portion of the distal end to the arm device, showing modified fingertip and thumb tip pockets

FIG. 8 shows the distal end of the arm device with abbreviated fingertip and thumb tip feature, which allows the wearer the roominess of a mitten and the fingertip control of a glove. The importance of this feature is to accommodate the hands that are enveloped in casting or bandage material, which includes partial or full finger coverage. This feature is previously unknown in the industry, as prior art allows for either a mitten device or a glove device, with full finger sleeves and a full thumb sleeve.

Figure 9:
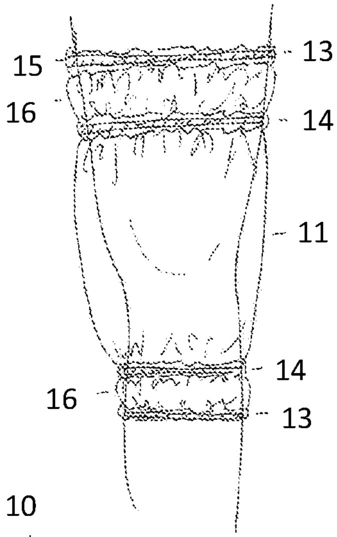
FIG. 9 illustrates the embodiment of the present invention, being tubular polymeric material, opened at both ends, in which both ends contain multiple encased elastic bands in the perspective of a mid-leg device.
Figure 10:
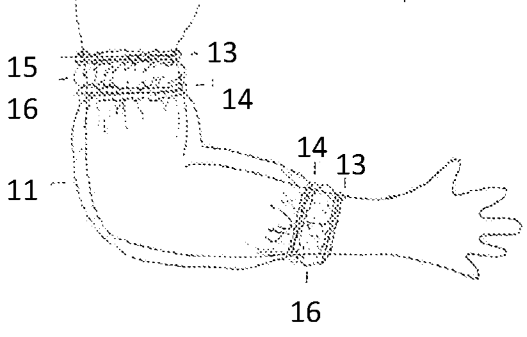
FIG. 10 illustrates the embodiment of the present invention, being tubular polymeric material, opened at both ends, in which both ends contain multiple encased elastic bands in the perspective of a mid-arm device.

The multiple encased elastic bands are placed at each open end of the device, as shown in FIG. 9 for the mid-leg device and FIG. 10 for the mid-arm device. This allows the wearer to apply the device over a central area of the affected limb while leaving the digits uncovered for hygienic purposes of bathing the hand or foot. This also pertains to devices designed for the torso.

Figure 11:
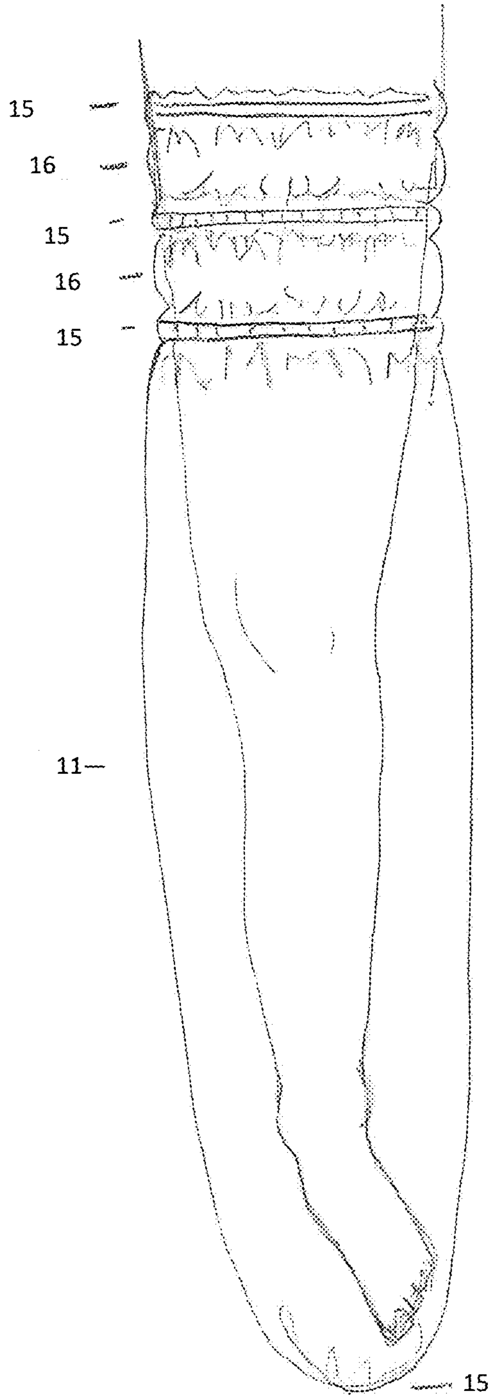
FIG. 11 illustrates the present invention with multiple self-encased elastic bands formed inward to produce a ledge.
Figure 12:
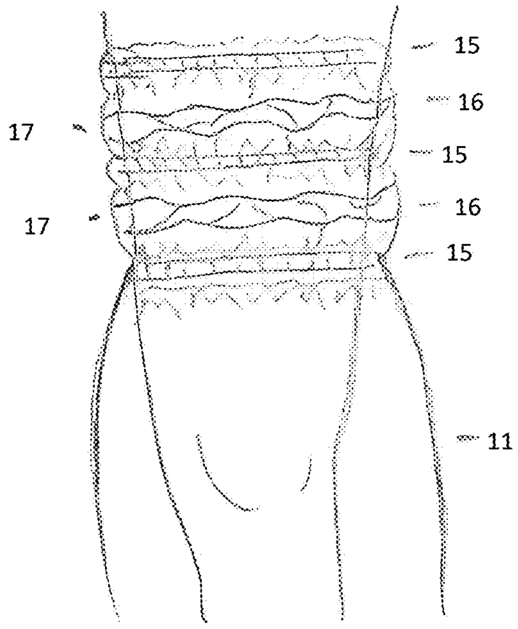
FIG. 12 illustrates the present invention with the insertion of absorbent material between the inwardly formed self-encased elastic bands.

FIG. 11 depicts multiple inwardly formed self-encased elastic bands to illustrate the number of bands can be increased as the need allows. FIG. 12 depicts the use of the absorbent material between the bands, and the importance of providing space between the ledges, which are formed inward within the self-casing to prevent wicking of water above or below the bands which would contaminate or damage the healing site.

What I claim as my invention is:

1. A waterproof covering for the purpose of showering with a cast, wound or bandage, comprising:

a proximal open end configured to surround a limb of a user and seal the limb within the covering such that the covering prevents entry of water in a shower setting;

a distal sealed end opposite the proximal open end on the covering, wherein the distal sealed end comprises a palmar portion and abbreviated fingertip and thumb tip pockets extending from the palmar portion, wherein the palmar portion is configured to receive a bandaged or casted hand of the user and the abbreviated fingertip and thumb tip pockets are configured to only contain the fingertips and thumb tip of the bandaged or casted hand of the user such that the bandaged or casted hand of the user adequately fits in the distal sealed end while the user is capable of making use of their fingertips to aid in a bathing process, wherein the distal sealed end of the covering is configured to provide roominess of a mitten and fingertip control of a glove for the hand enveloped in bandage or casting material having full finger coverage.

2. The waterproof covering of claim 1, wherein the covering further comprises a seamless, extruded polyethylene tube with non-slip properties produced by eliminating the slip property in the extrusion process and an anti-microbial agent integrated therein, wherein the tube has a circumference that is the same along an entire length of the tube.

3. The waterproof covering of claim 1, wherein the covering further comprises a plurality of encased, inwardly formed elastic bands spaced a distance parallel to each other and positioned near the proximal open end, wherein the space between each band is 2 inches and the space comprises a replaceable absorbent material disposed within.

4. The waterproof covering of claim 2, wherein the tube is stretchable and has a thickness of at least 1.5 mil.

5. The waterproof covering of claim 1, wherein the covering is configured to cover an arm and the hand of the user.

6. The waterproof covering of claim 1, wherein the abbreviated fingertip and thumb tip pockets are formed by heat sealing and die-cutting the tube.

7. The waterproof covering of claim 3, wherein the bands are encased within the tube by folding the tube and sealing the bands within.

8. The waterproof covering of claim 3, wherein the absorbent material comprises paper towels or facial cloths.

* * * * *